United States Patent [19]

Fung et al.

[11] Patent Number: 5,278,192
[45] Date of Patent: Jan. 11, 1994

[54] METHOD OF VASODILATOR THERAPY FOR TREATING A PATIENT WITH A CONDITION

[75] Inventors: Ho-Leung Fung, Getzville; John A. Bauer, Williamsville, both of N.Y.

[73] Assignee: Research Foundation of State University of NY, Albany, N.Y.

[21] Appl. No.: 908,224

[22] Filed: Jul. 2, 1992

[51] Int. Cl.$^5$ .............................................. A61K 31/13
[52] U.S. Cl. ..................................... 514/645; 514/509
[58] Field of Search ................. 514/645, 740, 506, 509

[56] References Cited

U.S. PATENT DOCUMENTS

| | | | |
|---|---|---|---|
| 3,106,511 | 10/1963 | Cuttler et al. | 514/509 |
| 4,450,175 | 5/1984 | Warshaw | 514/506 |
| 4,615,699 | 10/1986 | Gale et al. | 514/509 |
| 4,681,584 | 7/1987 | Gale et al. | 604/897 |
| 4,751,087 | 6/1988 | Wick | 514/509 |
| 4,956,181 | 9/1990 | Bayer et al. | 424/448 |

FOREIGN PATENT DOCUMENTS

0116944  8/1984  European Pat. Off. ...... A61K 31/21

OTHER PUBLICATIONS

Japanese Laid-Open Patent Publication No. 913 of 1983.
Japanese Laid-Open Patent Publication No. 185,919 of 1988.
Japanese Laid-Open Patent Publication No. 185,920 of 1988.
Japanese Laid-Open Patent Publication No. 156,909 of 1989.
L. A. Crandall, Jr., et al., "Acquired Tolerance To and Cross Tolerance Between the Nitrous and Nitric Acid Esters And Sodium Nitrite In Man," Oct. 6, 1930, pp. 103-119.
G. W. Burggraf, M.D., et al., "Left Ventricular Volume Changes After Amyl Nitrite and Nitroglycerin in Man as Measured By Ultrasound," Jan. 1974, pp. 136-143.
D. T. Mason, M.D., "The Effects of Nitroglycerin and Amyl Nitrite on Arteriolar and Venous Tone in the Human Forearm," Nov. 1965, pp. 755-766.
J. Ahlner, et al., "Organic Nitrate Esters: Clinical Use and Mechanisms of Actions," 1991, pp. 351 and 369.
G. R. Newell, M.D., et al., "Toxicity, Ummunosuppressive Effects and Carcinogenic Potential of Volatile Nitrites: Possible Relationship to Kaposi's Sarcoma," Sep./Oct., 1984, pp. 284-291.
B. Noack, "Mechanisms of Nitrate Tolerance-Influence of the Metabolic Activation Pathways," 1990, pp. 51-55.

(List continued on next page.)

*Primary Examiner*—S. J. Friedman
*Assistant Examiner*—William Jarvis
*Attorney, Agent, or Firm*—Nixon, Hargrave, Devans & Doyle

[57] ABSTRACT

The present invention provides a novel method of vasodilator therapy for treating a patient suffering from a condition, comprising long term, continuous administration of an organic nitrite to a patient suffering from the condition in a dosage form capable of delivering a sufficient therapeutic amount of nitrite to the blood stream of the patent thereby providing effective vasodilator therapy for at least 24 hours without development of tolerance in the patient. The method of the invention is useful in treating conditions such as, for example, angina, particularly chronic, stable angina pectoris, ischemic diseases, congestive heart failure, for controlling hypertension and/or impotence in male patients.

Any conventional drug delivery system can be employed in carrying out the method of the invention. The drug delivery system can take virtually as many different forms as there are dosage forms available for delivery of nitrite to a patient. For example, drug delivery systems within the scope of the invention include sublingual, oral and buccal tablets as well as capsules, topical creams and ointments, patches, tapes, spray and intravenous solutions.

18 Claims, 2 Drawing Sheets

OTHER PUBLICATIONS

E. Noack, et al., "Molecular Mechanisms of Nitrovasodilator Bioactivation," 1991, pp. 37-50.

M. Packer, M.D., FACC, "What Causes Tolerance to Nitroglycering? The 100 Year Old Mystery Continues," 1990, pp. 932-935.

J. Dupuis, M.D., et al., "Tolerance to Intravenous Nitroglycerin in Patients with Congestive Heart Failure: Role of Increased Intravascular Volume, Neurohumoral . . . ," 1990, p. 923.

J. P. Tarburton, et al., "Kinetics of Amyl Nitrite-Induced Hemoglobin Oxidation in Cord and Adult Blood," Mar. 2, 1985, pp. 15-21.

L. C. Green, et al., "Analysis of Nitrate, Nitrite, and [$^{15}$N]Nitrate in Biological Fluids", Feb. 22, 1982, pp. 131-138.

E. M. Dax, et al., "Amyl Nitrite Alters Human In Vitro Immune Function," 1991, pp. 577-587.

P. J. Henry, et al., "Nitrate Tolerance Induced by Nicorandil or Nitroglycerin is Associated with Minimal Loss of Nicorandil Vasodilator Activity," 1990, pp. 365-370.

Hop-Leung Fung, Ph.D., Pharmacokinetic Determinants of Nitrate Action, Jun. 22, 1984, The American Journal of Medicine, pp. 22-26.

Steven Corwin, M.D., James A. Reiffel, M.D., Nitrate Therapy for Angina Pectoris, Mar., 1985, Arch Intern Med-vol. 145, pp. 538-543.

Jonathan Abrams, M.D., Pharmacology of Nitroglycerin and Long-Acting Nitrates, Jul. 10, 1985, The American Journal of Cardiology, vol. 56, pp. 12A-18A.

John T. Flaherty, M.D., Hemodynamic Attenuation and the Nitrate-Free Interval: Alternative Dosing Strategies for Transdermal Nitroglycerin, Amer. Jou. of Card., Dec. 27, 1985, vol. 56, pp. 321-371.

Jonathan Abrams, Chapter 3, Mechanism of Actions of Nitrates, pp. 79-95, 1992.

T. Zimmermann, M. Leitold and R. Yeates, Comparison of isobutyl nitrate and isobutyl nitrite: tolerance and cross-tolerance to glyceryl trinitrate, Eur. Journ. of Pharm., Nov. 6, 1990, pp. 181-184.

Ho-Leung Fung and John Bauer, Effects of chronic glyceryl trinitrate on left ventricular . . . Cardiovascular Research, 1990, pp. 198-203.

Elizabeth Kowaluk and Ho-Leung Fung, Vascular Nitric Oxide-Generating Activities for Organic Nitrites and Organic Nitrates are Distinct, Journal of Pharm., vol. 259, No. 2, pp. 519-525, 1991.

J. Parker, M. D., B. Farrell, RN, T. Fenton, EdD, M. Cohanium, M.D., J. Parker, M.D., Counter-Regulatory Responses . . . Neurohormonal Resp. to Nitrogly. Cir., vol. 84, No. 6, Dec. 1991, pp. 2336-2345.

H. Fung, PhD, S. Chung, PhD, J. Bauer, PhD, S. Chong, PhD, and E. Kowaluk, PhD, Biochemical Mechanism of Organic Nitrate Action, The Amer. Journal of Cardiology, Sep. 1992, vol. 69, pp. 4B-10B.

P. Needleman and E. Johnson, Jr., Mechanism of Tolerance Development to Organic Nitrates, The Journal of Pharmacology, vol. 184, No. 3, 1973, pp. 709-715.

J. Diamond and T. Holmes, Effects of Patassium Chloride and Smooth Muscle Relaxants on Tension and Cyclic Nucleotide Levels in Rat Myometrium, Can. J. Physiol. Pharmacol., vol. 53, 1975, pp. 1099-1107.

S. Katsuki, W. Arnold and F. Murad, Effects of Sodium Nitroprusside, Nitroglycerin, and Sodium Azide on Levels of Cyclic Nucleotides . . . , Journal of Cyclic Nucleotide Res., pp. 239-247, 1977.

F. Murad, C. Mittal, W. Arnold, S. Katsuki and H. Kimura, Guanylate Cyclase: Activation by Azide, Nitro Compounds . . . , Advances in Cyclic Nucleotide Res., 1978, pp. 145-158.

L. Ignarro, H. Lippton, J. Edwards, W. Baricos, A. Hyman, P. Kadowitz and C. Gruetter, Mechanism of Vascular Smooth Muscle Relaxation by Organic Nitrates . . . , Jou. of Phar., vol. 218, No. 3, pp. 739-749, 1981.

J. Bauer and H. Fung, Differential Hemodynamic Effects and Tolerance Properties of Nitroglycerin and an S-Nitrosothiol in Experimental Heart Failure, Journal of Pharm., vol. 256, No. 1, pp. 249-256, 1990.

H. Fung, S. Chong and E. Kowaluk, Mechanisms of nitrate action and vascular tolerance, European Heart Journal, 1989 10, Supplemental A, pp. 2-6.

W. Levy, M.D., R. Katz, M.D., FACC, A Wasserman, M.D., FACC, Methionine Restores the Venodilative Response to Nitroglycerin After the Development of Tolerance, JACC, vol. 17, No. 2, Feb. 1991, p. 474.

R. Katz, M.D., W. Levy, M.D., L. Buff, RN, A. Wasserman, M.D., Prevention of Nitrate Tolerance With Tolerance With Angiotension Converting Enzyme Inhibitors, vol. 83, No. 4, Apr. 1991, pp. 1271-1277.

J. Bauer, MSc and H. Fung, PhD, Concurrent Hydralazine Administration Prevents Nitroglycerine-Induced Hemodynamic Tolerance in Exper. Heart Failure, Brief Rapid Comm. vol. 84, No. 1, Jul. 1991, pp. 35-39.

R. Lange, M. Reid, D. Tresch, M. Keelan, V. Bernhard, G. Coolidge, Nonatheromatous Isch. Heart Dis. following Withdrawal from Chronic Ind. Nitroglycerin Exp., Circulation, vol. XLVI, Oct. 1972, pp. 666-678.

M. Olivari, M.D., P. Carlyle, B.S., T. Levine, M.D., J. Cohn, M.D., FACC, Hemod. and Horm. Resp. to Transdermal Nitro. in Norm. Sub. and in Pat. with Cong. Heart Fail., JACC vol. 2, No. 5, Nov. 1983, 872-8.

Y. Lis, D. Bennett, G. Lambert, D. Robson, A preliminary double-blind study of intravenous nitro. in acute myocardial infarction, Inten. Care Med., 1984, pp. 179-184.

M. Packer, W. Lee, P. Kessler, S. Gottlieb, N. Medina, M. Yushak, Prevention and Reversal of Nitrate Tolerance in Pat. with Cong. Heart Failure, N. E. Jour. of Med., Sep. 24, 1987, vol. 317, No. 13, pp. 799-804.

U. Elkayan, A. Roth, B. Henriquez, L. Weber, D. Tonnemacher, S. Rahimtoola, Hemodyn. and Horm. Eff. High-Dose Trans. Nitro. Pat. with Chron. Con. Heart Fail., Sep. 1985, Amer. Jour. of Card. vol. 56, pp. 555-559.

S. Flaim, Peripheral vascular effects of nitroglycerin in a conscious rat model of failure, Amer. Physiological Soc., pp. H974-H981, 1982.

C. Leier, R. Magorien, C. Desch, M. Thompson, D. Unverferth, Hydralazine and Isosorbide Dinitrate: Comp. Central and Reg. Hemodyn. Eff. When Admin. Alone or in Comb., vol. 63, No. 1, Jan. 1981, pp. 102-109.

Curtis D. Black, Ph.D., Transdermal Drug Delivery Systems, U.S. Pharmacist, Nov. 1982, pp. 49-78.

H. Selye, E. Bajusz, S. Grasso, P. Mendell, Simple

OTHER PUBLICATIONS

Techniques for the Surgical Occlusion of Coronary Vessels in the Rat, pp. 398-407, 1960.

S. Flaim, S. Nellis, E. Toggart, H. Drexler, K. Kanda, E. Newman, Multiple Simult. Determ. of Hemody. and Flow Dist. in Conscious Rat, Journ. of Pharm. Methods, pp. 1-32, 1984.

J. Abrams, C. Pepine, U. Thadani, Medical Therapy of Ischemic Heart Disease; Nitrates, Beta Block, and Calcium Antagonists, Chap. 3, pp. 79, 95, 1992.

METHOD OF VASODILATOR THERAPY FOR TREATING A PATIENT WITH A CONDITION

This invention was made with support by the U.S. Government under grant No. 5R01GM42850 awarded by the National Institute Of General Medical Sciences. The Government has certain rights in this invention.

FIELD OF INVENTION

The present invention relates generally to drug therapy and, more particularly, to a method of vasodilator therapy for treating ischemic diseases, angina pectoris, hypertension and/or congestive heart failure.

BACKGROUND OF THE INVENTION

Congestive heart failure is a complex and heterogeneous disease state associated with decreased cardiac performance and increased pulmonary and peripheral oedema. Congestive heart failure results when the left, right or both ventricles fail to pump sufficient blood to meet the body's needs. An estimated 4 million people currently in the United States have congestive heart failure. While no single drug or drug class has proven to be ideal in treating this disease, vasodilator therapy constitutes a major approach in its clinical management.

Organic nitrate esters, such as nitroglycerin, isosorbide dinitrate, isosorbide-5-mononitrate, etc. are organic chemicals that contain the $ONO_2$ group. Nitrates are part of a family of vasodilators called nitrovasodilators and have enjoyed extensive use in cardiovascular therapy; but other members of this class, e.g., nitroprusside, molsidomine and organic nitrites are not organic nitrates. Nitrovasodilators such as isosorbide dinitrate and glyceryl trinitrate are useful in treating congestive heart failure because they cause a prompt reduction in preload and/or afterload, and relieve the venous congestion often associated with this disease.

Nitroglycerin, also referred to as trinitroglycerin or glycerin trinitrate, has also been used to treat angina pectoris for over 100 years. Nitroglycerin and other nitrovasodilators have been available for the treatment of angina pectoris and congestive heart failure in a number of different dosage forms for some time. These include sublingual, oral and buccal tablets as well as capsules, topical creams and ointments, patches, tapes, lingual sprays and intravenous solutions.

Transdermal nitroglycerin patches were introduced in recent years in an effort to overcome some of the disadvantages and inconveniences of other dosage forms. In particular, transdermal patches were formulated to provide increased systemic bioavailability as well as constant delivery of the drug over a 24 hour period or longer. Typically, the patches are applied once daily, either in the morning or evening, and changed daily at approximately the same time, and have become popular in the treatment of chronic, stable angina and congestive heart failure.

However, the positive effects of these patches are often short lived. For example, it has been shown that nitroglycerin produces rapid hemodynamic tolerance (within several hours) in congestive heart failure after continuous administration either by intravenous or transdermal routes. Intermittent dosing with a regimen of 12 hours on/12 hours off can avoid development of tolerance but the effect of the previous dose is lost within 2 hours of drug withdrawal, leaving the patient unprotected during the majority of the "dose-off" period. Furthermore, a more frequent on/off dosing strategy (4 or 8 hour on/off cycles) was not successful in avoiding tolerance development. At present no dosage regimen with nitrovasodilators has been developed that can achieve the dual objectives of avoidance of hemodynamic tolerance while continuously maintaining their beneficial effects.

Additionally, headaches typically accompany treatment with organic nitrates such as nitroglycerin. Headaches may be recurring with each daily dose, especially at higher doses. Aside from headaches, which may be severe and persistent, other adverse central nervous system (CNS) reactions include apprehension, restlessness, weakness, vertigo, dizziness and faintness.

DESCRIPTION OF THE RELEVANT MEDICAL LITERATURE

Recently, the results of a number of clinical studies have raised questions regarding the efficacy of chronic nitrate therapy due to the observed development of tolerance or haemodynamic attenuation during long term nitrate therapy in general and, in particular, nitrate therapy using transdermal patches. The following is a list of representative articles and patents from the medical literature, and a brief description of each:

(1) "Pharmacokinetic Determinants of Nitrate Action", Ho-Leung Fung, Ph.D., *The American Journal of Medicine*, Jun. 22, 1984, pages 22–26. The author states that the issue of nitrate tolerance in the clinical setting is controversial. He further speculates that the actual systemic concentration, as such, may be less important than the change in concentration with time producing beneficial effects from nitrates, and that "the rate of drug input may yet be another determinant of nitrate action." He postulates that an alternate input mode, particularly for transdermal nitroglycerin, "might be one that involves escalating rates of drug delivery so that increasing systemic nitrate concentrations may be achieved. If nitrate tolerance is a concern over 24-hour dosing period, then a drug washout period may be incorporated (most likely during the sleeping hours) . . ." He concludes that "the validity of this dosing approach has to be experimentally tested, and the potential problems arising from it (for example, control of nocturnal angina) are yet to be fully appreciated."

(2) "Nitrate Therapy for Angina Pectoris", Steven Corwin, MD, James A. Reiffel, MD, *Arch. Intern. Med.*, Vol. 145, Mar. 1985, pages 538–543. After reviewing the efficiency and mechanism of action of various nitrate preparations, the authors state that it is a matter of debate whether tolerance develops in patients receiving nitrates over long time periods, but suggest that the clinician should be aware of this possibility when using these agents.

(3) "Pharmacology of Nitroglycerin and Long-Acting Nitrates", Jonathan Abrams, MD, *Am. J. Cardiol.*, 1985, Vol. 56, pages 12A–18A. The author concludes the article with a discussion of nitrate tolerance in which he indicates that this remains "a vexing and difficult problem." He notes that there have been suggestions that providing sustained nitrate plasma concentrations or repeated administration of large doses may induce tolerance more readily than interrupted or lower dose therapy, and that this may be particularly relevant to transdermal nitroglycerin. He suggests that the clinician be prepared to change the nitrate dosage regimen when it appears that there may be tolerance-either discontinuing nitrates for "a short period of time or increas[ing] the dose, or both."

(4) "Nitrate Tolerance", John O. Parker, MD, *Am. J. Cardiol.*, 1985, Vol. 56, pages 281-311. The author reports that results of studies using both oral and transdermal isosorbide dinitrate and transdermal nitroglycerin as indicating that tolerance developed with long term administration in each case. However, short washout periods of as little as 9 hours between oral doses or transdermal patch applications seemed to avoid the tolerance effect in angina patients. He concludes that "it appears desirable to prescribe oral nitrates on a 3-times-a-day basis, with no medication after the supper dose. With transdermal preparations, one could postulate that it would be best to remove the patches after 12 or 16 hours of application to allow overnight washout."

(5) "Hemodynamic Attenuation and the Nitrate-Free Interval: Alternate Dosing Strategies for Transdermal Nitrogylcerin", John T. Flaherty, MD, *Am. J. Cardiol.*, 1985, Vol. 56, pages 321-371. This author also finds that his review of the data of other investigators suggest that clinically significant tolerance occurs with all forms of long-term nitrate therapy when administered continuously. He is uncertain whether higher doses administered continuously can overcome this effect, and asserts both that further testing is required, and that it seems equally likely that a nitrate-free interval, e.g. by interrupting administration during the night, might provide a means for avoiding tolerance. This could be accomplished, he suggests, by removing the patch at night and applying a new one in the morning, or in the case of oral, buccal or ointment preparations, omitting the last otherwise administered dose at the end of the day. This author also stresses the importance of dose titration in individual patients.

(6) Chapter 3, "Mechanism of Actions of Nitrates", Jonathan Abrams, from "Medical Therapy of Ischemic Heart Disease: Nitrates, Beta Blockers and Calcium Antagonists", Little, Brown and Company, Boston, 1992. This is a review on the use of nitrates as cardiac vasodilators.

(7) "Comparison of Isobutyl Nitrate and Isobutyl Nitrite: Tolerance and Cross-Tolerance to Glyceryl Trinitrate", Torsten Zimmermann, et al., *European Journal of Pharmacology*, 1991, Vol. 192, pp. 181-184. The author reports in vitro comparisons between isobutyl nitrate and isobutyl nitrite. He found in vitro cross-tolerance between organic nitrites and organic nitrates. In fact, he also found a 1.7 fold shift in the dose-response curve upon self-tolerance toward isobutyl nitrite, which was developed after 1 hour of pre-incubation with the compound itself.

(8) "Effects of Chronic Glyceryl Trinitrate on Left Ventricular Haemodynamics in a Rat Model of Congestive Heart Failure: Demonstration of a Simple Animal Model for the Study of In Vivo Nitrate Tolerance", John Anthony Bauer, et al., *Cardiovascular Research*, 1990, Vol. 24, pp. 198-203. The authors studied the effects of chronic glyceryl trinitrate infusions in a rat model of congestive heart failure, induced by myocardial infarction. It was concluded that the haemodynamic tolerance caused by glyceryl trinitrate resembled that seen in man and suggests a possible use for this animal model in examining the mechanisms of nitrate action and tolerance.

(9) "Vascular Nitric Oxide-Generating Activities for Organic Nitrites and Organic Nitrates Are Distinct", Elizabeth Kowaluk, et al., *Journal of Pharmacology and Experimental Therapeutics*, September 1991, Vol. 259, No. 2, pp. 519-525. The authors utilized subcellular fractions of the bovine coronary arterial smooth muscle to examine the potential for enzymatic conversion of organic nitrites to nitric oxide (NO); the subcellular location of such an activity; and its relationship to the NO-generating enzyme for nitroglycerin. They concluded that "results of this study suggest that dissimilar metabolic activation mechanisms for the organic nitrates and nitrites are associated with different in vitro vascular tolerance properties." That is, the NO-generating enzymes for the organic nitrites are distinct from the NO-generating enzyme for the organic nitrate, nitroglycerin.

(10) "Counter-Regulatory Responses to Continuous and Intermittent Therapy with Nitroglycerin", John D. Parker, et al., *Circulation*, Dec. 1991, Vol. 84, No. 6, pp. 2336-2345. The authors evaluated the effects of continuous and intermittent therapy with transdermal nitroglycerin (NTG) in a group of normal subjects (e.g., in vivo mechanism of tolerance). They concluded that continuous transdermal NTG therapy lead to counter-regulatory responses associated with sodium retention and probable plasma volume expansion. By contrast, intermittent transdermal NTG therapy was associated with a different pattern of hormonal responses, the lack of sodium retention and no evidence of plasma volume expansion. The authors stated that "although other mechanisms may well be involved in nitrate tolerance, it is likely that those counter-regulatory effects play an important role and their presence affords the possibility of devising new methods of preventing the development of tolerance to the hemodynamic effects of the organic nitrates.

(11) "Biochemical Mechanism of Organic Nitrate Action", Ho-Leung Fung, et al., *Am. J. Cardiol.*, in press. The authors describe the different in vitro and in vivo mechanisms of nitrate tolerance. They presented evidence to indicate that in vivo nitrate tolerance might be caused by neuro-hormonal compensation in the systemic circulation. This mechanism would not be present in experiments involving isolated blood vessels studied in vitro.

(12) U.S. Pat. No. 4,681,584, to Grale et al., discloses a high flux transdermal nitroglycerin therapeutic system which is capable of delivering nitroglycerin through intact skin at rates of 40 mg/cm$^2$hr, and preferably in the range of from 50-150 mg/cm$^2$hr.

(13) U.S. Pat. No. 4,956,181, to Buyer et al., discloses a method and device for treating angina pectoris and preventing tolerance to nitrate drugs. The treatment comprises administering drug therapy involving overnight drug-free wash-out periods followed by delivery of the nitrate at a steadily increasing rate during the day.

(14) U.S. Pat. No. 4,751,087, to Wick, discloses a pressure-sensitive adhesive tape for delivering nitroglycerin to skin.

SUMMARY OF THE INVENTION

The primary object of the present invention is to provide a new and improved method of vasodilator therapy, for example, in treating ischemic diseases, angina pectoris, congestive heart failure, impotence, and/or controlling hypertension, without development of hemodynamic tolerance in the patient.

We have now discovered that tolerance associated with conventional vasodilator therapy (i.e., nitrovasodilators) can be avoided while providing effective long term, continuous treatment. More particularly, the present invention provides a method of vasodilator therapy for treating a patient suffering from a condition, comprising long term, continuous administration of an organic nitrite to a patient suffering from the condition in a dosage form capable of delivering a sufficient therapeutic amount of a nitrite to the blood stream of the patient thereby providing effective vasodilator therapy for at least 24 hours without development of tolerance in the patient. The method of the invention is useful in treating conditions such as, for example, angina, particularly chronic, stable angina pectoris, ischemic diseases, congestive heart failure, for controlling hypertension and/or impotence in male patients.

In connection with the method of the invention, any conventional drug delivery system for carrying out the dosage form can be employed. It is understood that the drug delivery system can take virtually as many different forms as there are dosage forms available for delivery of nitrite to patients. For example, drug delivery systems within the scope of the invention include sublingual, oral and buccal tablets as well as capsules, topical creams and ointments, patches, tapes, lingual sprays and intravenous solutions.

DETAILED DESCRIPTION OF THE INVENTION

Figure 1:
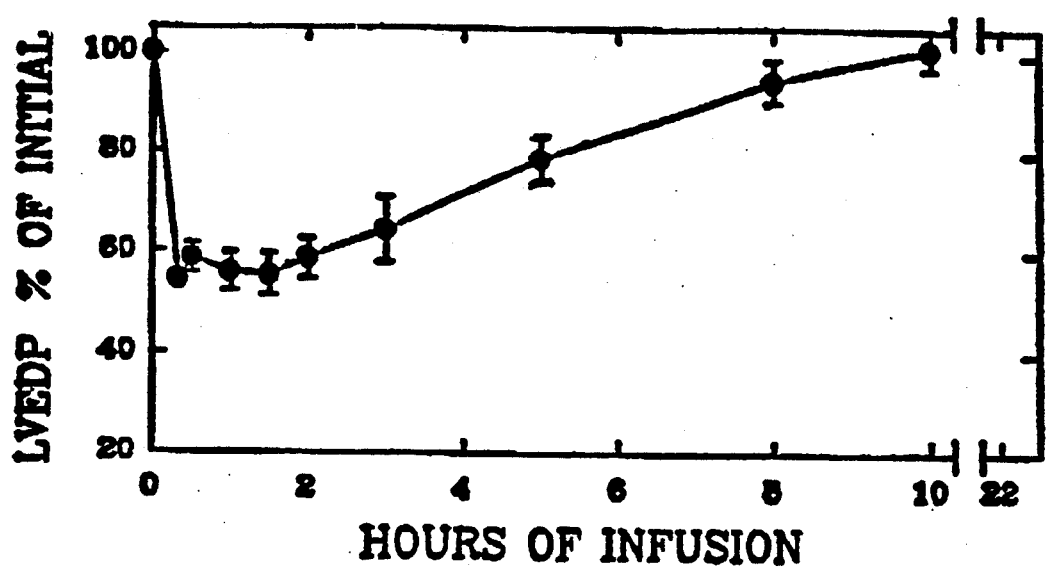
FIG. 1 is a graph illustrating the effects of continuous intravenous infusion (10–15 µg/min) of nitroglycerin to congestive heart failure rats. The pharmacologic effect measured was the left ventricular end-diastolic pressure.

The present invention provides a new vasodilator therapy for long term, continuous therapy, without tolerance development in the patient after at least 1 day. More particularly, there is provided a method for long-term continuous administration of an organic nitrite for treatment of a patient suffering from a condition such as, for example, chronic angina pectoris, controlling blood pressure in hypertension and especially hypertension associated with cardiovascular procedures, ischemic diseases, congestive heart failure or pulmonary edema associated with acute myocardial infarction and/or impotence in male patients. The organic nitrite can be administered in any know dosage form, for example, lingually, sublingually, intrabuccally, orally, topically, by inhalation or IV infusion.

The only known use of a nitrite for treating the above disease states is old, and, includes the use of amyl nitrite for the acute relief of angina pectoris, not for long term, continuous drug therapy. Furthermore, the drug is seldom if ever used today because it is expensive, inconvenient and has a high incidence of adverse effects and has an unpleasant odor.

For a better understanding of the present invention, it is first necessary to look at the tolerance problems associated with conventional nitrate therapy, the particular disease states to be treated and the biochemical mechanisms of organic nitrates and nitrites. Turning first to nitrate therapy, tolerance to the individual nitrates as well as cross-tolerance may occur with repeated, prolonged use. Tolerance to the vascular and antianginal effects of the drugs has been shown in clinical studies, by experience from occupational exposure, and in isolated in vitro tissue experiments. Such tolerance is a principal factor limiting the efficacy of long-term nitrate therapy. Tolerance to nitrates appears to be associated with high and/or sustained plasma drug concentrations and frequent administration, i.e. continuous therapy. Rapid development of tolerance has occurred with oral, IV, and topical nitrate therapy (i.e., transdermal systems or nitroglycerin ointment). Tolerance to the pharmacologic effects is generally minor with intermittent use of sublingual nitrates. Furthermore, some evidence suggests that the development of tolerance can be prevented or minimized by use of the lowest effective dose of nitrates and an intermittent dosing schedule with a nitrate free interval of 10–12 hours (e.g., removal of a transdermal nitroglycerin system in the early evening and application of a new system the next morning or omission of the last daily dose of oral, buccal, or topical [ointment]nitrate preparations). However, the minimum nitrate-free interval necessary for restoration of full first-dose effects of nitrate therapy has not been determined. Additionally, the intermittent dosing schedule leaves the patient exposed to the potential risks of the condition during the "off" periods.

Adverse reactions to nitrate therapy, regardless of form of dosage mainly involve the cardiovascular system. Headache, the most frequent adverse effect, may be severe (persistent or transient) and is perceived as a pulsating, throbbing sensation. Furthermore, postural hypotension may occur in patients receiving nitrates which may cause dizziness, weakness and other signs of cerebral ischemia. Some patients may have a marked sensitivity to the hypotensive effects of the nitrates and nausea, vomiting, weakness, restlessness, pallor, cold sweat, tachycardia, syncope and cardiovascular collapse may occur with therapeutic doses. In addition, in patients receiving transdermal delivery, peripheral edema rash and/or dermatitis may occur.

Now turning to the various disease states, in one embodiment of the invention, nitrite therapy can be used in treating chronic, stable angina pectoris as well as unstable angina and silent ischemia. Angina pectoris is a symptom of myocardial ischemia that is usually secondary to coronary heart disease. "Angina pectoris" as used herein, means a sense of discomfort arising in the myocardium as a result of myocardial ischemia in the absence of infarction. Angina usually implies severe chest pain or discomfort. Coronary heart disease is the leading cause of death and disability in the United States and angina is the first clinical sign of this disease in about one-third of men and two-thirds of women. Patients who have a reproducible pattern of angina that is associated with a certain level of physical activity have chronic, stable angina. In contrast, patients with unstable angina are experiencing new angina or a change in their angina pattern, frequency or duration.

In another embodiment herein, nitrite therapy can be used for treating hypertension. Hypertension as used herein, is a cardiovascular disease characterized by elevation of blood pressure above arbitrary values considered "normal" for people of similar racial and environmental background. Hypertension affects the vasculature of all major organ systems (e.g., heart, brain, kidneys), and myocardial infarction and congestive heart failure (CHF) account for the majority of deaths secondary to hypertension (i.e., hypertension is a major etologic factor in development of CHF). The morbidity and mortality that is associated with hypertension, increases linearly with higher systolic and diastolic blood pressures. The vast majority (e.g., about 85-90%) of individuals with hypertension have essential or primary hypertension which has no established cause. Hypertension is currently treated using thiazide diuretics and/or beta blockers when combined with non-drug interventions.

In still another embodiment of the invention, nitrite therapy can be used for treating congestive heart failure (CHF). CHF results when the left, right or both ventricles fail to pump sufficient blood to meet the body's needs. Increased cardiac workload and impaired myocardial contractility are important factors which contribute to the development of CHF. There are four major determinants which contribute to the left ventricular workload: preload, afterload, contractility and heart rate. Preload is the term to describe forces acting on the venous side of the circulation to affect myocardial wall tension. As venous return (i.e., blood flowing into the heart) increases, the volume of blood in the left ventricle increases. This increased volume raises the pressure within the ventricle (left ventricle end-diastolic pressure (LVEDP) which in turn increases the "stretch" or wall tension of the ventricle. An elevated preload will aggravate congestive heart failure. Afterload is the tension developed in the ventricular wall as contraction (systole) occurs. Afterload is regulated by the resistance or impedance against which the ventricle must pump during its ejection and is chiefly determined by arterial blood pressure. Contractility describes the inherent ability of the myocardium (cardiac muscle) to develop force and/or shorten independent of preload or afterload.

When the heart begins to fail, the body activates several complex compensatory mechanisms in an attempt to maintain cardiac output and oxygenation of vital organs. These include cardiac (ventricular) dilation, cardiac hypertrophy, increased sympathetic tone and sodium and water retention. Nitrate vasodilator therapy has been used to manage CHF unresponsive to the body's mechanisms and other traditional therapy, however, the problems associated with hemodynamic tolerance, as previously mentioned, and other adverse side effects render this therapy inadequate.

It will become apparent to one skilled in the art that the present invention of using nitrites as vasodilators in the chronic management of various disease states is unobvious when taking into account the bio-mechanisms of nitrate therapy which is discussed in detail hereinafter. The principal pharmacologic property of nitrates is relaxation of vascular smooth muscle, resulting in generalized vasodilation. Peripheral venous resistance is decreased via a selective action on venous capacitance vessels and results in venous pooling of blood and decreased venous return to the heart. The vasodilatory effect of the drugs on arteriolar resistance is not as great as the action on the venous side. As a result of this combined action, both venous filling pressure (preload) and, to a lesser extent, arterial impedance (afterload) are reduced. Left ventricular end-diastolic pressure (LVEDP) and volume (LVEDV) are decreased resulting in reduction of ventricular size and wall tension, particularly in patients with occlusive coronary artery disease and especially after exercise, atrial pacing or added fluid load. It is worth noting that although the nitrates reflexly increase heart rate and myocardial contractility which increase myocardial oxygen consumption, the reduction in ventricular wall tension results in a net decrease in myocardial oxygen consumption. By decreasing myocardial oxygen consumption, nitrates alter the imbalance of myocardial oxygen supply and consumption, which is thought to cause angina pectoris. In addition, the nitrates may increase total coronary blood flow secondary to coronary vasodilation in patients with normal hearts. In patients with ischemic hearts, nitrates may cause a beneficial redistribution of coronary blood flow resulting in decreased myocardial ischemia.

Our current understanding of the biochemical mechanism of organic nitrate action in vitro is owed principally to three major findings. First, Needleman et al., "Mechanism of Tolerance Development to Organic Nirtates", *J. Pharmacol Exp. Ther.*, 1973, Vol. 184, pp. 709-715, which disclosure is hereby incorporated by reference, demonstrated that the vasodilating action of nitrates are critically dependent on the availability of reduced sulfhydryl groups, and the pharmacological tolerance to their vasodilating effects may arise from intracellular sulfhydryl depletion. Second, Diamond et al., "Effects of Potassium Chloride and Smooth Muscle Relaxants on Tension and Cyclic Nucleotide Levels in Rat Myometrium", *Can. J. Physiol. Pharmacol*, 1975, Vol. 53, pp. 1099-1107; and Murad et al., "Effects of Sodium Nitroprusside, Nitroglycerin, and Sodium Azide on Levels of Cyclic Nucleotides and Mechanical Activity of Various Tissues", *Adv. Cyclic Nucleotide Res.*, 1977, Vol. 3, pp. 239-247, which disclosures are hereby incorporated by reference, showed that the pharmacologic action of many nitrovasodilators is mediated through the activation of the enzyme guanylate cyclase, resulting in an accumulation of intracellular cyclic guanosine 3', 5'- monophosphate (cyclic GMP). Since nitric oxide (NO) is an active stimulator of guanylate cyclase as shown by Murad et al., "Guanylate Cyclase: Activation by Azide, Nitro Compounds, Nitric Oxide and Hydroxyl Radical and Inhibition by Hemoglobin and Myoglobin", *Adv. Cyclic Nucleotide Res.*, 1978, Vol. 9, pp. 145-158, which disclosure is hereby incorporated by reference, it was reasoned that nitrovasodilators act through the production of NO.

Third, in the early 1980's, Ignarro et al., "Mechanism of Vascular Smooth Muscle Relaxation by Organic Nitrates, Nitrites, Nitroprusside and Nitric Oxide: Evidence for the Involvement of S-Nitrosothiols as Active Intermediates", *J. Pharmacol. Exp. Ther.*, 1981, Vol. 218, pp. 739-749, which disclosure is hereby incorporated by reference, extended the above concepts and suggested that sulfhydryl groups react with NO, an end product of nitrate metabolism, to form S-nitrosothiols which then activate guanylate cyclase.

Through the above studies, a widely recognized biochemical cascade describing the in vitro mechanism of nitrate action has been formulated as follows: (1) Organic nitrates first interact with sulfhydryl groups to produce nitric oxide (or S-nitrosothiols); (2) these compounds then activate quanylate cyclase to produce cyclic GMP, which then causes vasodilation; and (3) nitrate tolerance, both in vitro and in vivo, is derived from intracellular sulfhydryl depletion, which reduces the metabolic conversion of organic nitrates to NO, and thereby vasodilation.

However, this mechanism of nitrate action and, in particular, the relevance of this mechanism for the development of in vivo tolerance has been recently questioned and expanded. Bauer and Fung in "Differential Haemodynamic Effects and Tolerance Properties of Nitroglycerin and an S-Nitrosothiol in Experimental Heart Failure", *J. Pharmacol. Exp. Ther.*, 1990, Vol. 256, pp. 249-254, which disclosure is hereby incorporated by reference, suggested that the formation of S-nitrosothiols may not be obligatory for organic nitrate action. The criterion for defining whether sulfhydryl groups are critical for nitrate action is whether exogenous supplementation of sulfhydryl sources would either potentiate nitrate action, or reverse the pharmacologic tolerance that has been induced. The reverse criterion, e.g., whether depletion of sulfhydryl sources would decrease nitrate action and induce tolerance, is less frequently applied and has only been carried out in in vitro preparations. In Fung et al., "Mechanism of Nitrate Action and Vascular Tolerance", *Eur. Heart. Jr.*, 1989, Vol. 10 (Supp. A), pp. 2-6, which disclosure is hereby incorporated by reference, it was found that while addition of sulfhydryl compounds indeed can potentiate the in vitro and in vivo action of nitrates in a number of preparations, this is by no means universally observed. Recent evidence suggests that both sulfhydryl generating (Levy et al., "Methionine Restores the Venodilative Response to Nitroglycerin After the Development of Tolerance", *J. Am. Col. Cardiol.*, 1991, Vol. 17, pp. 474-479, which disclosure is hereby incorporated by reference) and non-sulfhydryl compounds (Katz et al., "Prevention of Nitrate Tolerance with Angiotension Converting Enzyme Inhibitors", *Circulation* 1991, Vol. 83, pp. 1271-1277; and Bauer et al., "Concurrent Hydralazine Administration Prevents Nitroglycerin Induced Haemodynamic Tolerance in Experimental Heart Failure", *Circulation*, 1991, Vol. 84, pp. 35-39, which disclosures are hereby incorporated by reference) can prevent the occurrence of in vivo nitroglycerin induced tolerance. These results suggest that the availability of reduced sulfhydryl groups can facilitate the vasodilating action of organic nitrates, but that tolerance development (particularly in vivo) may not result from sulfhydryl depletion.

The fact that addition of exogenous sulfhydryl sources may reverse nitrate tolerance is not, by itself, a sufficient and necessary criterion that sulfhydryl depletion occurs during such tolerance development. Sulfhydryl compounds, therefore, appear to regulate the pharmacologic action of organic nitrates. However, despite widespread acceptance of the concept, it is still unclear how much the phenomenon of intracellular sulfhydryl depletion indeed contributes to the occurrence of nitrate tolerance in the clinical setting.

While it is possible to invoke the sulfhydryl depletion hypothesis to explain the occurrence of pharmacologic tolerance induced by organic nitrates, it is difficult to use the same mechanism to rationalize another known effect of these drugs, i.e., that of nitrate rebound. It has long been known that munitions workers develop what are called "Monday headaches" after temporary withdrawal of nitrate exposure during the weekend, and that some individuals may even develop ischemic heart disease following withdrawal from chronic nitroglycerin exposure, as described by Lange et al., "Non-Atheromatous Ischemic Heart Disease Following Withdrawal from Chronic Industrial Nitroglycerin Exposure," *Circulation* 1972, Vol. 46, pp. 666-678, which disclosure is hereby incorporated by reference. Olivari et al., "Hemodynamic and Hormonal Response to Transdermal Nitroglycerin in Normal Subjects and in Patients with Congestive Heart Failure," *J. Am. Coll. Cardiol.*, 1983, Vol. 2, pp. 872-878, which disclosure is hereby incorporated by reference, examined the hemodynamic responses to transdermal NTG in patients with congestive heart failure. They showed that after NTG removal, each patient exhibited a transient decrease in cardiac index, along with a transient increase in pulmonary and systemic arterial pressures, and pulmonary, systemic and forearm vascular resistances. These rebound phenomena are consistent with the development of counter-regulatory vaso-constrictive forces during nitrate therapy.

Several studies have suggested that systemic biochemical changes also occur during nitrate tolerance. Lis et al., "A preliminary Double-Blind Study of Intravenous Nitroglycerin Acute Myocardial Infarction", *Intensive Care Med.*, 1984, Vol. 10, pp. 179-184, which disclosure is hereby incorporated by reference, observed that during a 48 hour intravenous NTG administration to patients with acute myocardial infarction, both the hemoglobin concentration and packed cell volume were reduced, suggesting a potential increase in plasma volume. In their study, Olivari et al., as described elsewhere herein, did not find accompanying changes in plasma renin and catecholamine levels in patients with congestive heart failure during either the NTG treatment or rebound periods, but in normal subjects, they did find peripheral vasodilation to be accompanied by reflex sympathetic stimulation as reflected by an increase in heart rate and plasma norepinephrine. Packer et al., "Prevention and Reversal of Nitrate Tolerance in Patients with Congestive Heart Failure", *New Eng. J. Med.*, 1987, Vol. 317, pp. 799-804, which disclosure is hereby incorporated by reference, showed that when patients with congestive heart failure were infused with NTG for 48 hours, hemodynamic tolerance developed, and this was accompanied by significant increases in plasma renin activity as well as body weight.

In contract, Elkayam et al, "Haemodynamic and Hormonal Effects of High-Dose Transdermal Nitroglycerin in Patients with Chronic Congestive Heart Failure", *Am. J. Cardiol.*, 1985, Vol. 56, pp. 555-559, which disclosure is hereby incorporated by reference, showed no apparent changes in serum catecholamine and renin concentrations after transdermal NTG application in patients with congestive heart failure, even though rapid attenuation of a mild effect on pulmonary artery wedge pressure was seen. It must be pointed out, however, that the lack of changes of plasma levels or neurohormonal factors is not, in itself, a sufficient argument against the neurohormonal mechanism of nitrate tolerance. First of all, plasma neurohormonal levels are influenced by many sources, including synthesis, release, and degradation. Thus, plasma levels may not properly reflect changes in the pertinent tissue compartments. Secondly, tissue response toward circulating neurohormonal stimulation is based not only on the concentrations of these agents, but also (among other factors) on receptor density and binding capacity as well. Preliminary evidence suggests potential alterations in receptor and ion channel density and/or activity in the left ventricle and in vascular segments during intermittent and continuous NTG administration in a rat model of heart failure. Thus, physiologic receptor responses may be altered even though plasma neurohormonal concentrations may appear unchanged.

Other studies also appear to support systemic biochemical compensation, rather than vascular sulfhydryl depletion, as an in vivo mechanism of nitrate tolerance. Katz et al., described elsewhere herein, recently showed that enalapril, a non-sulfhydryl ACE inhibitor, is capable of preventing the development of tolerance to the venodilating effects of NTG in normal volunteers. It was also shown that co-administration of hydralazine can avert the development of NTG-induced tolerance to its LVEDP effects in experimental heart failure (See Bauer and Fung, described elsewhere herein). Since hydralazine did not prevent the development of NTG-induced vascular tolerance in vitro, nor did it affect NTG pharmacokinetics in vivo, it appears reasonable to suggest that this beneficial effect might arise from a systemic, rather than vascular, interaction. In the same experimental model of heart failure, Flaim "Peripheral Vascular Effects of Nitroglycerin in a Conscious Rat Model of Heart Failure", *Am. J. Physiol.*, 1982, Vol. 243, pp. H974–H981, which disclosure is hereby incorporated by reference, showed that NTG infusion produced decreases in renal blood flow by about 20%. Leier et al., "Hydralazine and Isosorbide Dinitrate: Comparative Central and Regional Haemodynamic Effects When Administered Alone or in Combination", *Circulation* 1981, Vol. 63, pp. 102-14 109, which disclosure is hereby incorporated by reference, also observed that isosorbide dinitrate decreased renal blood flow, while hydralazine increased it. It was surmised, therefore, that NTG-induced tolerance might arise from reduced perfusion of the kidneys during chronic NTG dosing, leading to the production of counter-regulatory neurohormonal factors to maintain adequate renal blood flow. Both the ACE inhibitors and hydralazine can prevent the development of nitrate tolerance presumably because they can interrupt or counteract this process.

Organic nitrites which can be used in the present invention, include any organic nitrite ester. For example, such organic nitrites can include isobutyl nitrite, isoamyl nitrite, glyceryl trinitrite, glyceryl dinitrite (1,2- or 1,3-), glyceryl mononitrite, isosorbide dinitrite or mononitrite, isoidide dinitrite or mononitrite, isomannide dinitrite or mononitrite, pentaerythrityl tetranitrite, trinitrite, dinitrite or mononitrite, etc., or the like or combinations thereof. Many organic nitrite esters are extremely volatile and flamable liquids, practically insoluble in water and miscible with alcohol, and thus are difficult to work with in a laboratory settihg. Accordingly, organic nitrites would not be the choice of chemicals to look to for developing vasodilators. Because of the volatility of organic nitrites, they could first be diluted in a stabilizer or the like.

In accordance with the present invention, the dosage of nitrite is preferably a daily dosage amount adequate to provide the necessary protection or relief to the patient from congestive heart failure, angina pectoris and/or hypertension symptoms. It is understood that the absolute amount will vary with the patient, the particular nitrite employed, and the dosage form to be administered. Also, these parameters will affect the delivery rates or fluxes employed in the drug delivery system utilized. For purpose of example only, various dosage forms are described hereinafter in detail. However, it is apparent that the dosages will vary based on the above parameters.

In accordance with one embodiment of the invention, when a transdermal nitrite patch is employed, it is preferably applied at the same time each day to areas of clean, dry, hairless skin of the upper arm or body; the units should not be applied to the extremities below the knee or elbow. Skin areas with irritation, extensive scarring or calluses should be avoided, and application sites should be rotated to avoid potential skin irritation. The usual initial adult dosage is 1 transdermal patch applied every 24 hours. The total nitrite delivered from a single patch (unit dosage) will be in the range of from about 1 to about 100 mg/day, preferably from about 2 to about 60 mg/day, and more preferably from about 5 to about 30 mg/day for the typical patient. It is understood that transdermal nitrite drug delivery can be effected either through application of a gel or ointment (described hereinafter) to the skin or through the use of various commercially available transdermal delivery systems. A reasonable survey of transdermal products which can employ the organic nitrite in accordance with the invention are described by Curtis Black, "Transdermal Drug Delivery", *U.S. Pharmacist*, Nov. 1982, pp. 49–75, which disclosure is hereby incorporated by reference. Additionally, exemplary patents relating to delivery systems include U.S. Pat. Nos. 4,191,015; 3,742,951; and 4,191,015; 3,742,951 and 4,262,003 which disclose using a permeation enhancer to control delivery rates, which disclosures are hereby incorporated by reference.

The nitrite can also be applied topically as an ointment. The ointment is spread on any non-hairy skin area (usually the chest or back) in a thin, uniform layer without massaging or rubbing and using applicator paper typically supplied by the manufacturer. To protect clothing, plastic wrap held in place by an elastic bandage, tape or the like can be used to cover the ointment. The amount of nitrite reaching the circulation varies directly with the size of the area of application and the amount of ointment applied. The ointment is typically spread over an area approximately equivalent to 3.5 by 2.25 inches or greater (6 by 6 inches). A suggested initial dosage is 0.5 inch, squeezed from the tube, of the 2% ointment (approximately 7.5 mg.) every 8 hours. When the dose to be applied is in multiples of whole inches, unit-dose preparations that provide the equivalent of 1 inch of the 2% ointment can be used. Dosages should be titrated upward until angina is effectively controlled or adverse effects preclude further increases. In the treatment of congestive heart failure (CHF), an initial dose of about 1.5 inches of 2% nitrite ointment can be used and gradually increased in 0.5 to 1-inch increments up to a dosage of 4 inches every 4–6 hours. Again, the dosage should be titrated upward until CHF is controlled.

In accordance with another embodiment of the invention, the treatment is accomplished by an oral delivery system, the particular dosage form being selected from capsules, caplets, tablets and similar pharmaceutically acceptable oral dosage forms. When an oral dosage form is employed, the unit dose will be selected to deliver to the patient from about 2.5 to about 300 mg/day of nitrite, preferably from about 5 to about 160 mg/day, preferably, the entire daily unit dosage will be provided in one or two sustained release capsules, caplets or tablets designed to provide the desired drug delivery profile as described herein. Alternatively, combinations of different oral delivery dosage forms and strengths can be employed to achieve the desired drug delivery profile.

In accordance with still another embodiment of the invention, treatment of chronic, angina pectoris can be accomplished by sublingual and/or buccal dosages. For long-term treatment, nitrite extended-release buccal (transmucosal) tablets can be placed on the oral mucosa between the lip and gum above the upper incisors or between the cheek and gum. The tablet should be allowed to dissolve undisturbed. The initial dosage is preferably about 1 mg 3 times daily given every 5 hours during waking hours and dosage should be titrated upward incrementally until angina is effectually controlled. Preferably, for long-term treatment of angina pectoris, about 1.3–9 mg. of nitrite as an extended-release formulation can be administered orally about every 8 or 12 hours.

In accordance with still another embodiment of the invention, treatment of congestive heart failure can be accomplished by IV dosage. When nitrite therapy is administered by IV, it should be diluted with a suitable stabilizer before administration. The type of IV administration set used, polyvinyl chloride (PVC) or non PVC should be considered in dosage estimations. When non-PVC administration sets are used, the initial adult IV dosage of 5 $\mu$g/minute is recommended, with increase of 5 $\mu$g/minute every 3–5 minutes until a blood pressure response is obtained and then the dosage should be titrated by increments of about 10 $\mu$g/minute until the appropriate blood pressure response and/or chest pain decreases. When PVC administration sets are used, high dosages are generally required, with an initial adult dosage of about 25 $\mu$g/min.

The following examples are presented to further illustrate the present invention.

EXAMPLE I

Rat Model of Conoestive Heart Faiure

Congestive heart failure was produced in rats secondary to ligation of the left coronary artery, similar to the technique of Selye et al., "Simple Techniques for the Surgical Occlusion of Coronary Vessels in the Rat", Angiology, 1960, Vol. II, pp. 398–407, which disclosure is hereby incorporated by reference. Male Sprague-Dawley rats (300–325 grams) were anaesthetized with a combination of Innovar (0.3 ml kg$^{-1}$ intramuscularly, Pitman-Moore, Washington Crossing, N.J.) and diazepam (2.0 mg kg$^{-1}$ intramuscularly), then orally intubated and maintained by a Harvard rodent ventilator (Harvard Apparatus, South Natick, Mass.). A left thoracotomy was made at the fifth intercostal space, and the pericardium was gently torn. The left coronary artery was then ligated by an intramural suture (6-0 silk) placed just below the left atrium, approximately 3 mm from the origin. Vessel occlusion was ascertained by the paling of the ventricle distal to the suture. The lungs were then hyperinflated and the ribs closed by three interrupted sutures. The entire thoracotomy region was then swabbed with antibacterial ointment, and the muscle and skin layers were closed using an uninterrupted purse string suture. These animals were then allowed to recover for at least 6 weeks, producing a fully healed myocardial infarct. Complete occlusion of the left coronary artery in surviving rats typically produced a transmural infarct at the apex and anterior free wall of the left ventricle. Overall mortality of this procedure was approximately 40% during the 6–8 week recovery.

EXAMPLE II

Rats were anaesthetized with halothane 1.5–2.0% in oxygen and maintained via a Harvard rodent ventilator. The right cartoid artery was isolated. A fluid filled (saline with 10 units ml$^{-1}$ haperain) length of polyethylene tubing (PE-50, Clay-Adams, Parsippany, N.J.) with a slightly tapered tip and no bevel was inserted and advanced to the left ventricle, approximately 2 mm past the aortic valve. The tapered tip was intended to minimize valvular damage during insertion. Proper placement of the catheter was assured by monitoring pressure waveforms detected by a Statham P231D pressure transducer (Gould, Cleveland, Ohio) and displayed on a Narco Biosystems Physiograph (Narco Biosystems, Houston, Tex.). The catheter was firmly secured and brought through a subcutaneous tunnel to the dorsal cervical region. The neck incision was then closed using a purse string suture.

To allow detachment of the transducer from the rat, so as to facilitate repeated haemodynamic measurements and instrument recalibration over many hours, a fluid filled needle hub/PRN adapter (Deseret Medical, Sandy, Utah) assembly was devised. This adapter was attached to the PE-50 catheter and securely sutured to the back of the neck. This system was similar in design and function to a marketed product developed for similar purposes by Vascular Assess Port, Norfolk Medical Products, Skokie, Ill. Left ventricular pressures were easily measured by penetrating the rubber septum of the PRN adapter assembly with a needle tipped length of PE-50 (fluid filled) which was connected to the transducer. No dampening of these pressure tracings occurred provided air bubbles were carefully avoided. Tracings using the needle hub/PRN adapter assembly were identical to the initial tracings made using a continuous length of tubing of comparable length (35–40 cm). Prior to recording ventricular pressures, the physiograph was properly calibrated using an identical needle hub/PRN adapter system and a pressure manometer placed at the approximate height of the animals head. Determinations of left ventricular and diastolic and peak systolic pressures were carried out by calculating the mean of at least 30 consecutive tracings. Baseline haemodynamic measurements were made at least 3 hours after termination of halothane according to Flaim, et al., "Multiple Simultaneous Determinations of Haemodynamics and Flow Distribution in Conscious Rat", J. Pharmacol. Meth., 1984, Vol. II, pp. 1–39, which disclosure is hereby incorporated by reference, and their average values were calculated from at least 3 sets of tracings recorded over 30 minutes. This technique of left heart catheterisation provided continuous measurement of stable left ventricular pressures typically for 2 days and often for as long as 5–6 days. Failure of the catheter system, when it occurred, was most commonly due to fouling of the tip within the left ventricle.

EXAMPLE III

Nitrglycerin Infusion

Prior to left ventricular catheterisation, a polyethylene catheter (PE-50) was placed in the left femoral vein of the rat and tunneled subcutaneously to the base of the neck. Nitroglycerin (NTG) solution 1.0 mg/ml, Schwarz Pharma GmbH, Germany, was infused via this catheter using a Harvard infusion pump at a flow rate of 10–15 µg/min. Glass syringes were used for NTG infusion to avoid drug absorption. Rats with congestive failure (as previously described) were infused with NTG continuously for a period of 10 hours. Left ventricular pressures were measured in conscious, unrestrained rats periodically throughout the infusion experiment.

With reference to FIG. 1, the effects of continuous, long term infusion of NTG in congestive heart failure rats is shown. Pressure tracings were detected using high fidelity microtransducer and recorded by a Gould physiograph. The results show that intravenous infusion caused initial reduction in left ventricular end-diastolic pressure, but this effect is not maintained during continuous infusion for 10 hours, indicating the development of tolerance. Data is expressed as mean±(SEM), n=10–15.

EXAMPLE IV

Isobutyl Nitrite Infusion

Infusion was carried out as described in Example 1, except that the rats with congestive heart failure were infused with isobutyl nitrite (ISBN), instead of nitroglycerin, continuously for a period of 24 hours. Left ventricular pressures were measured in conscious, unrestrained rats periodically throughout the infusion experiment.

Figure 2:
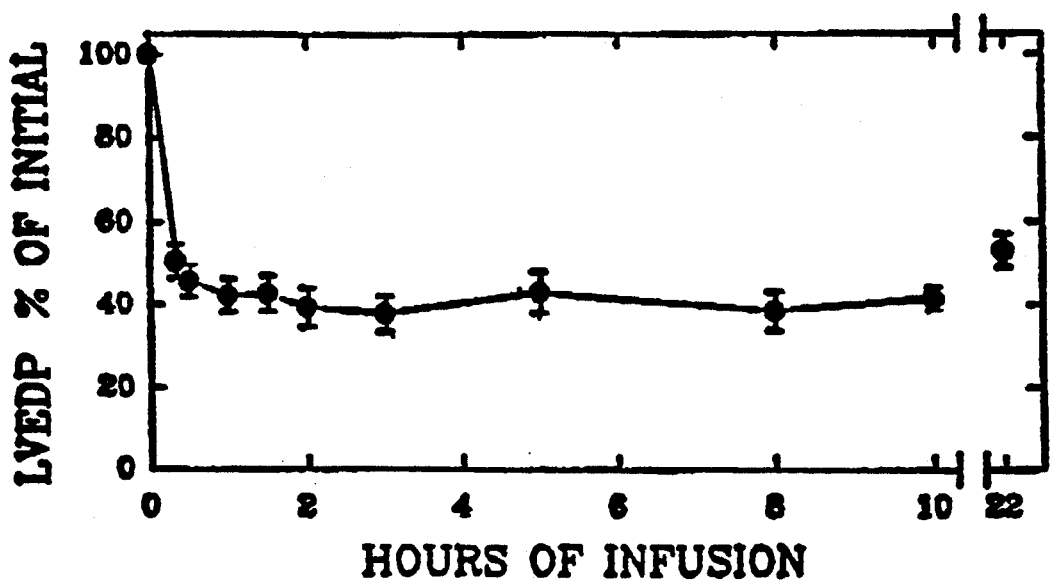
FIG. 2 is a graph illustrating the effects of continuous intravenous infusion (3.13 or 5.0 µl/hr) of isobutyl nitrite to congestive heart failure rats. The pharmacologic effect measured was the left ventricular end-diastolic pressure (LVEDP).

With reference to FIG. 2, the effects of continuous, long term infusion of ISBN to congestive heart failure rats is shown. Intravenous infusion (3.13 or 5.0 µl/hr) caused rapid initial reductions in left ventricular end-diastolic pressure, and these initial effects were maintained throughout the infusion period, most significantly, even after 24 hours of continuous infusion. These results demonstrate that ISBN can be a useful and novel vasodilator, without tolerance development within the first 24 hours as was seen after just about 2 hours for infusion with nitroglycerin (FIG. 1).

EXAMPLE V

Transdermal Administration

A 2% ointment of isobutyl nitrite (ISBN) in petrolatum was prepared. Approximately 500 mg of the ointment was then applied to the shaved abdomen of an anesthetized rat. Arterial blood pressure and heart rate was measured in the rat before and during ointment application. It was observed that ointment application caused a reduction in blood pressure after 35 minutes of ointment application. The average blood pressure over 30 minutes prior to ointment treatment was 108/83 mmHg. At 35–40 minutes after application, blood pressure was 93/68 mmHg. These results suggest that ISBN is capable of being absorbed transdermally at concentrations significant to produce a vasodilator effect and they are consistent with the high lipophilicity of ISBN.

EXAMPLE VI

Isoamyl Nitrite Infusion

Infusion was carried out as described in Example 1, except that the rats with congestive heart failure were infused with isoamyl nitrite, instead of nitroglycerin, continuously for a period of 24 hours. Left ventricular pressures were measured in conscious, unrestrained rats periodically throughout the infusion experiment.

Figure 3:
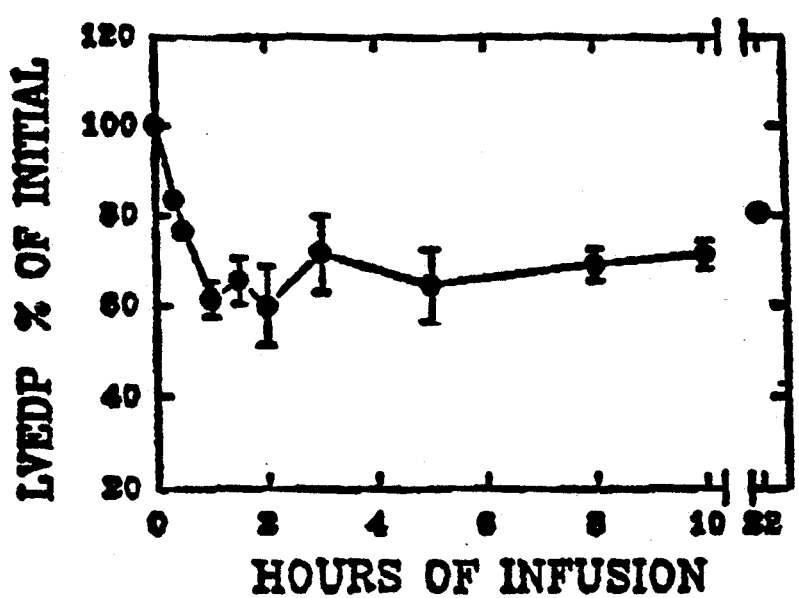
FIG. 3 is a graph illustrating the effects of continuous intravenous infusion (3.13 µl/hr) of isoamyl nitrite to congestive heart failure rats. The pharmacologic effect measured was the left ventricular end-diastolic pressure (LVEDP).

With reference to FIG. 3, the effects of continuous, long term infusion of isoamyl nitrite to congestive heart failure rats is shown. Intravenous infusion (3.13 µl/hr) caused rapid initial reductions in left ventricular end-diastolic pressure, and these initial effects were maintained throughout the infusion period, most significantly, even after 24 hours of continuous infusion. These results demonstrate that isoamyl nitrite can be a useful and novel vasodilator, without tolerance development within the first 24 hours as was seen after just about 2 hours for infusion with nitroglycerin (FIG. 1).

EXAMPLE VII

Effect of Nitrite Therapy on the Central Nervous System

It was observed that during nitrite therapy, a lack of apparent effects on the central nervous system of the rats occurred. During nitroglycerin infusion, the rats invariably became lethargic and they would not eat, drink or move about in their cages. These behaviors, which disappeared rapidly after the drug was withdrawn, likely are reflective of the known side-effects of nitroglycerin i.e., the occurrence of headache in patients. When rats with heart failure were infused with nitrites, at doses which produced comparable hemodynamic effects as nitroglycerin, the rats appeared normal and carried out their routine activities. These observations suggest that nitrites may not cause the undesirable effects on the central nervous system that are produced by nitroglycerin and other nitrates.

It is understood that the Examples described herein are for purposes of illustration only and, not limitation, and that various modifications and/or changes that may suggest themselves to one skilled in the art are intended to be included within the spirit of this application and the scope of the appended claims.

We claim:

1. A method of vasodilator therapy for treating a patient suffering from a condition, comprising:
    long term, continuous administration of an organic nitrite selected from the group consisting of isobutyl nitrite and isoamyl nitrite to a patient suffering from the condition in a dosage form capable of delivering a sufficient therapeutic amount of said nitrite to the blood stream of the patient thereby providing effective vasodilator therapy for at least 24 hours without development of tolerance in the patient.

2. The method of claim 1, wherein said dosage form is a transdermal delivery system.

3. The method of claim 2, wherein said transdermal delivery system is selected from the group consisting of a patch, tape, ointment and topical cream.

4. The method of claim 1, wherein said dosage form is intravenous infusion.

5. The method of claim 1, wherein said dosage form is selected from the group consisting of sublingual, oral and buccal.

6. The method of claim 5, wherein said dosage form is a tablet or capsule.

7. The method of claim 2, wherein said transdermal system is a patch.

8. The method of claim 7, wherein the dosage administered to the patient from said patch is at least 2 mg/day.

9. The method of claim 8, wherein the dosage administered to the patient from said patch is between 5 and 100 mg/day.

10. The method of claim 1, wherein said organic nitrite is further characterized by lower volatility and increased stability.

11. The method of claim 1, wherein said condition is angina pectoris.

12. The method of claim 1, wherein said condition is congestive heart failure.

13. The method of claim 1, wherein said condition is hypertension.

14. The method of claim 1, wherein said condition is ischemic disease.

15. The method of claim 1, wherein said condition is impotence.

16. The method of claim 1, wherein said condition is unstable angina.

17. The method of claim 1, wherein said dosage is delivered to the patient at a constant rate.

18. The method of claim 1, wherein said patient shows no signs of central nervous system disorders.

* * * * *